(12) United States Patent
Wigh et al.

(10) Patent No.: US 12,733,850 B2
(45) Date of Patent: Sep. 15, 2026

(54) SMALL VOLUME COLLECTION CONTAINER

(71) Applicant: Becton, Dickinson and Company, Franklin Lakes, NJ (US)

(72) Inventors: Shruti Wigh, Maywood, NJ (US); Arun U. Nair, Denville, NJ (US); Michael Baker, Oradell, NJ (US); Syed Zulfiqar Abbas Zaidi, Kinnelon, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 852 days.

(21) Appl. No.: 17/686,844

(22) Filed: Mar. 4, 2022

(65) Prior Publication Data

US 2022/0280080 A1 Sep. 8, 2022

Related U.S. Application Data

(60) Provisional application No. 63/157,452, filed on Mar. 5, 2021.

(51) Int. Cl.
*A61B 5/15* (2006.01)

(52) U.S. Cl.
CPC .. *A61B 5/150343* (2013.01); *A61B 5/150022* (2013.01)

(58) Field of Classification Search
CPC ........ A61B 5/150343; A61B 5/150022; A61B 5/150259; A61B 5/150351; A61B 5/150755; B01L 3/5082; B01L 3/50825
See application file for complete search history.

(56) References Cited

U.S. PATENT DOCUMENTS

| | | | | |
|---|---|---|---|---|
| 5,455,009 | A | 10/1995 | Vogler et al. | |
| 6,426,049 | B1 | 7/2002 | Rosen et al. | |
| 8,806,920 | B2 | 8/2014 | Blekher et al. | |
| 2003/0133844 | A1* | 7/2003 | Conway | B01L 3/50825 422/400 |
| 2005/0065454 | A1 | 3/2005 | Manoussakis | |
| 2006/0115385 | A1 | 6/2006 | Jon Meyer et al. | |
| 2009/0259145 | A1 | 10/2009 | Bartfeld et al. | |
| 2011/0178424 | A1 | 7/2011 | Wilkinson et al. | |
| 2013/0252345 | A1 | 9/2013 | Wilkinson et al. | |
| 2015/0366543 | A1 | 12/2015 | El-Fahmawi | |
| 2016/0114318 | A1* | 4/2016 | Knight | G01N 35/10 422/549 |
| 2016/0278680 | A1 | 9/2016 | Bauer et al. | |

(Continued)

FOREIGN PATENT DOCUMENTS

| | | | |
|---|---|---|---|
| CN | 107233111 | A | 10/2017 |
| EP | 0901823 | A2 | 3/1999 |

(Continued)

*Primary Examiner* — Samuel P Siefke
(74) *Attorney, Agent, or Firm* — The Webb Law Firm

(57) ABSTRACT

A specimen collection container assembly including a collection tube having a first open end and a second open end, and an interior reservoir formed within the collection tube. The assembly further includes a cap configured to be couplable to the collection tube to close the first open end, as well as a plug configured to be couplable to the collection tube to close the second open end. The collection tube also includes a flat mouth portion extending 360° around the first open end.

16 Claims, 12 Drawing Sheets

(56) References Cited

U.S. PATENT DOCUMENTS

2016/0341641 A1 11/2016 Williams et al.
2018/0125464 A1* 5/2018 Kolb ...................... A61B 10/02
2018/0242572 A1 8/2018 Coddaire et al.
2019/0350508 A1 11/2019 Noguchi et al.

FOREIGN PATENT DOCUMENTS

JP H07167858 A 7/1995
JP 2001057969 A 3/2001
JP 2005095621 A 4/2005
JP 2008284400 A 11/2008
JP 2011215020 A 10/2011
JP 2013517509 A 5/2013
JP 2016518588 A 6/2016
JP 2019503654 A 2/2019
WO WO-2011041703 A2 * 4/2011 ........... G01N 1/4005
WO 2019054862 A1 3/2019

* cited by examiner 12
42
44
45
41
47
48
46
40

B
B
13

PUSH ON
TWIST OFF

SMALL VOLUME COLLECTION CONTAINER

CROSS-REFERENCE TO RELATED APPLICATIONS

The present application claims priority to U.S. Provisional Application No. 63/157,452, titled "Small Volume Collection Container" filed Mar. 5, 2021, the entire disclosure of which is hereby incorporated by reference in its entirety.

BACKGROUND OF THE INVENTION

Field of the Invention

The present disclosure relates to a small volume capillary specimen collection container assembly for the collection, storage, and transfer of a blood or specimen sample obtained from a patient for medical diagnostic testing. More specifically, the present disclosure relates to a container assembly for capillary collection and small volume venous blood processing of blood samples from a skin surface of the patient. The container assembly includes a collection tube having a flat, 360° lip feature surrounding a top opening of the tube suitable for collecting samples from a skin surface. The device also includes a specimen collection container assembly configured for use with automated clinical laboratory processes.

Description of Related Art

Conventional capillary collection devices according to the prior art typically provide a microtube or collection container having a raised receiving lip or funnel feature that engages the skin surface of a patient that has been pierced so as to draw a blood sample from the capillaries located just beneath the skin surface. The internal collection cavities of such prior art collection containers are typically straight-walled. Thus, a significant amount of the collected blood or specimen sample is caught on the sidewall of the cavity due to surface tension during collection and during transfer.

After collection, these tubes are sealed by a cap assembly disposed on the collection container. Conventional cap assemblies provide a flat bottom surface in communication with the collection cavity. As a result, a significant amount of dead volume of sample is created within the collection cavity during transfer since neither the collection container nor the cap assembly adequately funnel or channel the collected blood sample to the aspiration hole of the probe needle. As can be appreciated, conventional prior art collection devices create a significant amount of wasted sample and require a significantly higher volume of sample to be collected than what is actually needed to perform the diagnostic tests for which the sample is being collected. Sample volumes are particularly important in capillary applications, where a very small volume of blood is typically collected and/or available, and therefore avoiding any waste and/or providing improved instrument access to the sample volume is particularly important.

Additionally, due to their form factor and shorter accessible sample column height, automated processing and/or sample collection of conventional prior art collection containers utilizing a gel-based separation device has been difficult.

In addition, clinical laboratory processes using specimen collection containers have become increasingly automated. As such, many conventional capillary specimen collection containers are not compatible with automated front end processes used to prepare a specimen for proper analysis, such as sorting specimen collection containers by type and/or contents, adding features to specimen collection containers superficially or with additives specific to the contents of the specimen collection container, centrifugation, vision-based specimen quality analysis, serum level analysis, decapping, aliquoting, and automated labeling of secondary tubes. In addition, many conventional capillary specimen collection containers are not compatible with automated analyzing procedures and are not dimensioned to accommodate automated diagnostic and/or analyzing probes or other specimen extraction equipment. Further, many conventional capillary specimen collection containers are not compatible with certain automated back end processes employed after a specimen is analyzed, such as resealing, storage, and retrieval.

SUMMARY OF THE INVENTION

Accordingly, a need exists for a capillary specimen collection container having an improved mouth or opening to allow for easy blood droplet acquisition and containment, as well as improved automation compatibility. Additionally, there is a need for an improved tube reservoir which allows for easy collection of the acquired sample, as well as reliable barrier separation of a small volume blood sample via, e.g., a gel separator.

In addition, a further need exists for a specimen collection container that is compatible with automated clinical laboratory processes, including front end automation, automated analyzers, and/or back end automation, which provides for improved workflow efficiencies over conventional manual processing.

In accordance with an embodiment of the present disclosure, a specimen collection container assembly is provided. The specimen collection container includes a collection tube having a first open end and a second open end, an interior reservoir formed within the collection tube, and a cap configured to be couplable to the collection tube to close the first open end. The specimen collection container assembly also includes a plug configured to be couplable to the collection tube to close the second open end, wherein the collection tube further includes a flat mouth portion extending 360° around the first open end.

In some embodiments, the interior reservoir tapers from the first open end to a rounded bottom surface formed within the collection tube.

In some embodiments, the collection tube further includes a scoop portion formed within an interior wall surface proximate the flat mouth portion.

In some embodiments, the scoop portion is one of V-shaped, U-shaped, S-shaped, or reverse S-shaped.

In some embodiments, the plug is configured to be coupled to the collection tube by way of an interference fit.

In some embodiments, the plug is configured to be coupled to the collection tube way a snap-fit connection.

In accordance with another embodiment of the present disclosure, a specimen collection tube is provided. The specimen collection tube includes a first open end, a second open end, an exterior sidewall, and an interior reservoir formed within the exterior sidewall. The specimen collection tube further includes a flat mouth portion extending 360° around the first open end, and a scoop portion formed within an interior wall surface proximate the flat mouth portion.

In some embodiments, the interior reservoir tapers from the first open end to a rounded bottom surface.

In some embodiments, the scoop portion is one of V-shaped, U-shaped, S-shaped, or reverse S-shaped.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

Figure 1:
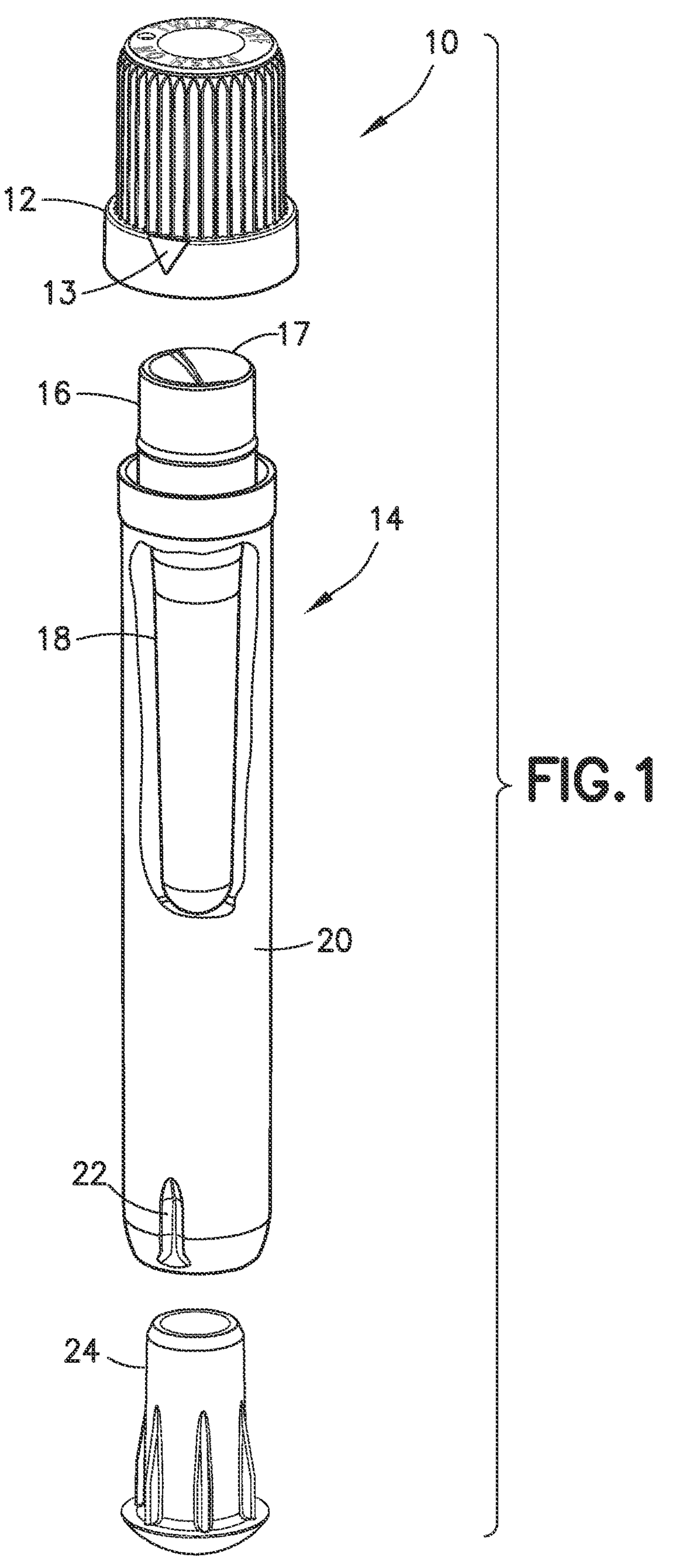
FIG. 1 is an exploded perspective view of a capillary collection container assembly for collecting blood samples in accordance with an aspect of the present disclosure.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present disclosure.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Referring to FIG. 1, a capillary collection container assembly 10 for collecting blood samples in accordance with an aspect of the present disclosure is shown. Collection container assembly 10 includes a collection tube 14 for the collection, storage, and eventual transfer of biological specimens, including blood samples, for purposes of diagnostic testing. A cap 12 is disposed on the collection tube 14 so as to cover and seal the collection tube 14 and any sample contained therein. According to the embodiment shown, cap 12 is removably disposed and attachable to the collection tube 14 after collection of the sample contained therein. In some embodiments, a shoulder or bottom annular portion of the cap 12 may include a cap alignment indicator 13. The cap alignment indicator 13 may be used to guide the user to properly align the cap 12 with the collection tube 14 in order to aid secure closure of the cap 12 on the collection tube 14, thereby ensuring specimen security. In some embodiments, an alignment indicator feature may be present on the collection tube 14, as well, either molded into the collection tube 14 or provided on a tube label.

The collection tube 14 may be a biological specimen collection container for proteomics, molecular diagnostics, chemistry sampling, blood or other bodily fluid collection, coagulation sampling, hematology sampling, and the like. In one embodiment, the collection tube 14 can be particularly suited for receipt and storage of a bodily fluid specimen. In a further embodiment, the collection tube 14 is particularly suited for receipt and storage of blood, such as venous blood or capillary blood, from a patient. As used herein, the term "patient" means a mammalian organism, and the collection tube 14 of the present disclosure is intended for use in specimen collection procedures performed on humans and/or animals.

Referring still to FIG. 1, collection tube 14 is a microtube suited for capillary collection of blood samples having overall exterior dimensions conforming to a standard tube (e.g., 13 mm×90 mm) so as to be compatible with standard testing instruments and/or automation processes. Collection tube 14 may be formed by, e.g., injection molding, from suitable plastic or composite material as is known to be suitable by those of ordinary skill in the art.

Collection tube 14 is defined by an exterior sidewall 20 extending from an open tube bottom 22 to an open lip portion 17. As will be described in further detail below, collection tube 14 includes upper mouth portion 16 and an internal reservoir 28 defined by a tapered sidewall 18. In some embodiments, internal reservoir 28 has an overall increased height-to-diameter ratio so as to create a taller column of blood or specimen within the collection tube 14, even when the volume of blood or specimen collected is relatively low (e.g., 800 μL or less), as compared to a conventional container having an internal reservoir having a constant diameter and straight walls. Providing a taller column of blood or specimen makes it easier for a medical professional or diagnostician to discern the volume of blood or specimen contained within the collection tube 14 in order to determine the amount of blood or specimen collected or available. Additionally, a taller column of blood or specimen within internal reservoir 28 further enables reliable barrier separation of the blood or specimen components by way of, e.g., a gel separator that is positioned post-centrifugation. Furthermore, providing a taller column of blood or specimen reduces the "dead volume", i.e., the volume of blood or specimen lost or left behind in the tube during direct aspiration from the tube. Increase in the column height may also allow the tube to be compatible with certain sample volume detection systems that may be part of various front end automation systems. Additionally and/or alternatively, the column geometry may also account for aspiration probe and tip diameters, allowing for successful probe travel with minimal opening or side wall contact.

Additionally, capillary collection container assembly 10 may further include a bottom plug 24. Bottom plug 24 is configured to be coupled to the collection tube 14 to effectively close the open tube bottom 22. In this way, collection tube 14 having an internal reservoir 28 may be easily formed by, e.g., injection molding, yet still maintain the form factor of more conventional collection tubes. That is, bottom plug 24 may be configured to provide collection tube 14 with a closed, rounded bottom to enable use of the collection tube 14 with existing automated racks and carriers. In some embodiments, the bottom plug 24 is configured for a press-fit interference connection to the collection tube 14 within open tube bottom 22. As will be described in further detail below, various characteristics may be provided on the bottom plug 24 so as to provide for such a secure interference connection.

Figure 2A:
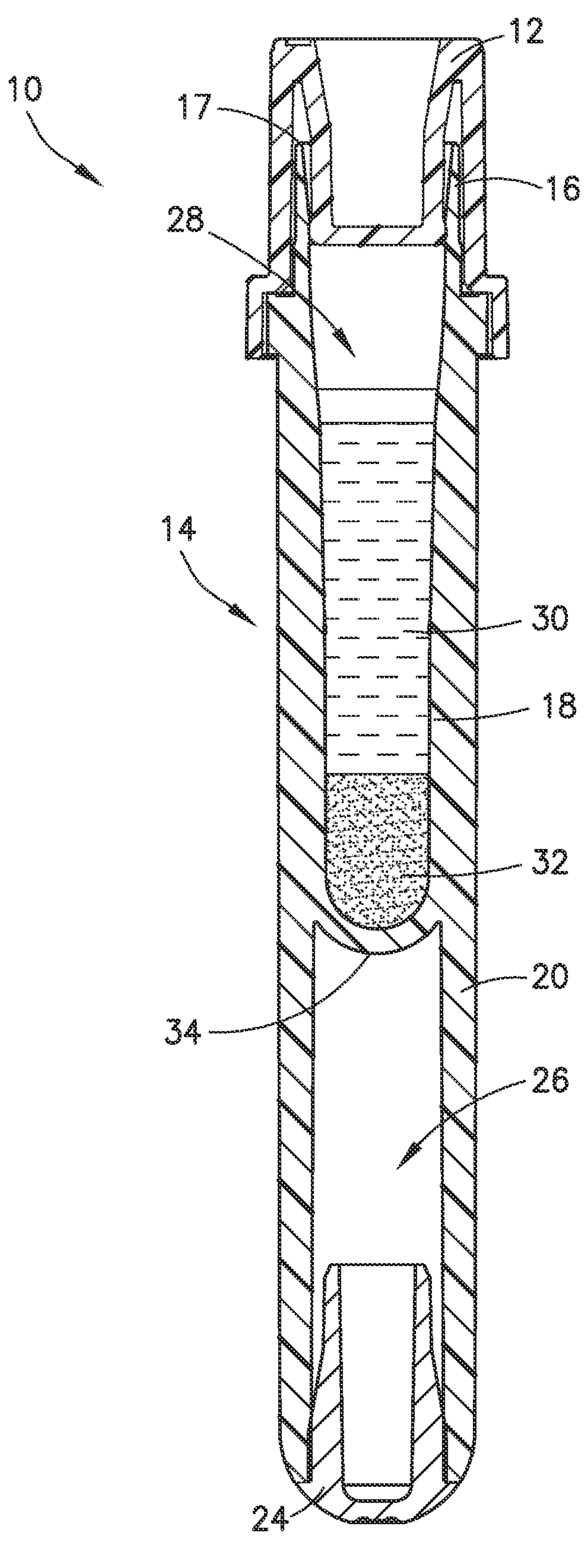
FIG. 2A is side cross-sectional view of the capillary collection container assembly of FIG. 1 in a pre-centrifugation condition.
Figure 2B:
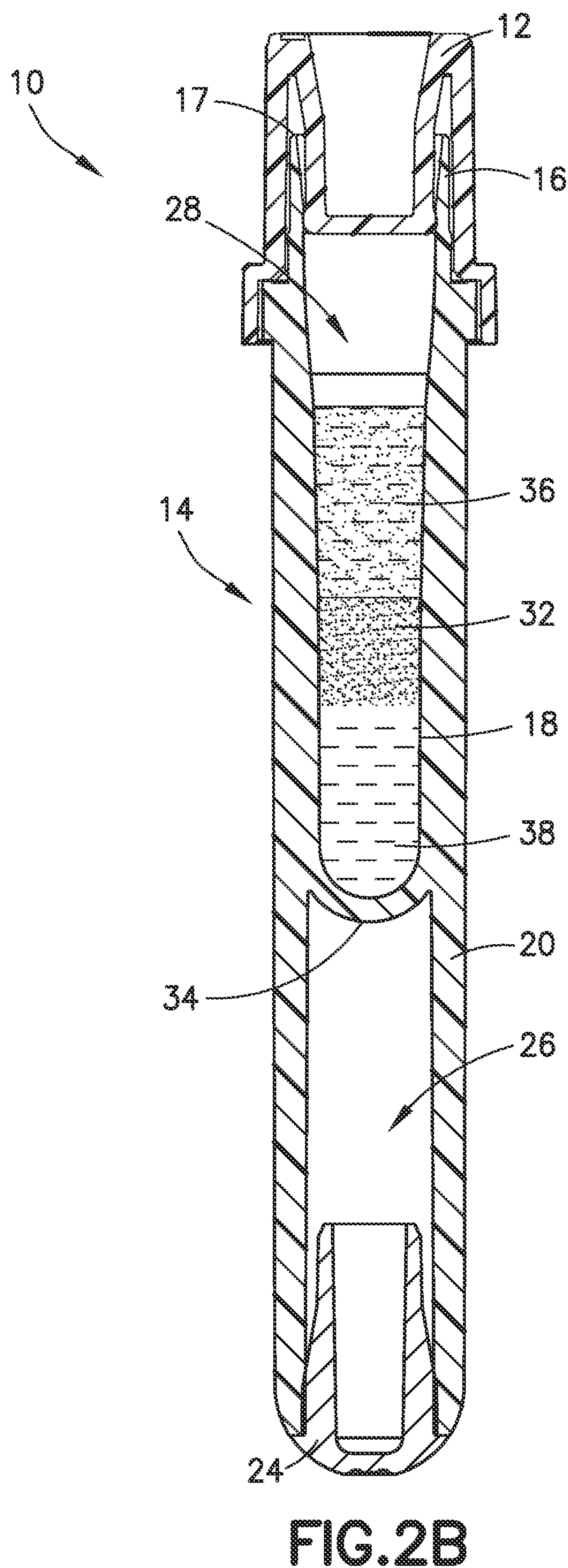
FIG. 2B is another side cross-sectional view of the capillary collection container assembly of FIG. 1 in a post-centrifugation condition.

Referring to FIGS. 2A and 2B, cross-sectional views of the collection container assembly 10 in both a pre-centrifugation state (FIG. 2A) and a post-centrifugation state (FIG. 2B) are shown. As shown in FIG. 2A, the cap 12 is configured to be coupled to the collection tube 14 about the upper mouth portion 16 so as to effectively close and seal the internal reservoir 28. As described above, an upper portion of the collection tube 14 defines the internal reservoir 28 for the collection, containment, and eventual transfer of biological specimens. Internal reservoir 28 extends from a rounded bottom 34 to the open lip portion 17 of the collection tube 14. In some embodiments, the internal reservoir 28 may be coated with one or more additives (e.g., a clot activator, lithium heparin, a hemorepellancy additive, etc.) that is sprayed or otherwise injected into the collection tube 14 for preserving a blood or specimen sample contained within the collection tube 14 during storage or for other diagnostic purposes as is known by those of ordinary skill in the art.

Internal reservoir 28 is defined within the sidewall 18, with sidewall 18 having a generally angled and rounded profile terminating in rounded bottom 34. As noted above, the angled and rounded profile of internal reservoir 28 allows for an overall increased height-to-diameter ratio so as to create a taller column of blood or specimen within the collection tube 14, thereby providing for better visualization and/or simplified collection of the specimen collected within internal reservoir 28, reduced "dead volume", compatibility with sample volume detection systems, etc. For example, in some embodiments, the interior sidewall 18 of the internal reservoir 28 may be angled between 2.5° to 10° relative to a central axis of the collection tube 14 from the rounded bottom 34 to the open lip portion 17, thereby providing for a taller specimen column as compared to a tube having an internal reservoir whose sidewalls are not angled (or minimally angled). Additionally, probe access may be improved by providing an outward taper or angle from the open lip portion 17 to the rounded bottom 34.

Referring still to FIGS. 2A and 2B, the lower portion of the collection tube 14 includes a generally hollow or "false" bottom cavity 26 defined by the exterior sidewall 20, the open tube bottom 22, and the rounded bottom 34 of the collection tube 14. The "false" bottom cavity 26 of the lower portion of the collection tube 14 assists in injection molding of the collection tube 14 by promoting plastic flow. Furthermore, by extending the lower portion of the collection tube 14 in this way, and also by providing bottom plug 24 in the open tube bottom 22, collection container assembly 10 may be more readily compatible with standard medical testing instruments and/or automation processes.

As noted above, FIG. 2A portrays collection container assembly 10 in a pre-centrifugation state according to one aspect of the disclosure. In such a state, the internal reservoir 28 may contain a gel separator substance 32 at a bottom portion thereof, and a specimen sample 30 (e.g., a blood sample) having an overall lower density than the gel separator substance 32 is maintained above the gel separator substance 32.

As is known in the art, upon centrifugation of such a collection container holding, e.g., a blood sample, the primary components of the blood (i.e., the plasma/serum and the hematocrit comprised primarily of red blood cells) separate by density, with the more dense hematocrit settling at the bottom of the internal reservoir, and the less dense plasma/serum collecting thereabove. A gel separator substance, meanwhile, is configured to have a density between that of the plasma/serum and hematocrit. Accordingly, upon centrifugation, the gel separator substance forms a barrier between the plasma/serum and the hematocrit. While a gel separator substance is shown and described herein, it is to be understood that any suitable type of separator, such as a mechanical separator, or separation using gel-microbead combination may also be utilized in accordance with some embodiments of the present disclosure.

For example, referring to FIG. 2B, collection container assembly 10 in a post-centrifugation state is shown. The blood sample 30 shown and described with respect to FIG. 2A separates into two primary component parts in the post-centrifugation state, those parts being the plasma/serum portion 36 and the hematocrit portion 38. Furthermore, after centrifugation, the gel separator substance 32 migrates from the bottom portion of the internal reservoir 28 to create an effective barrier between the plasma/serum portion 36 and the hematocrit portion 38. Due to the overall reduced size of the internal reservoir 28 in relation to the size of the entire collection tube 14, along with the tapered sidewall 18 of the internal reservoir 28, the plasma/serum portion 36 of the specimen sample 30 is easily visible to the user and accessible for analyzer/probe aspiration, even when the volume of collected capillary blood is relatively low.

Figure 3:
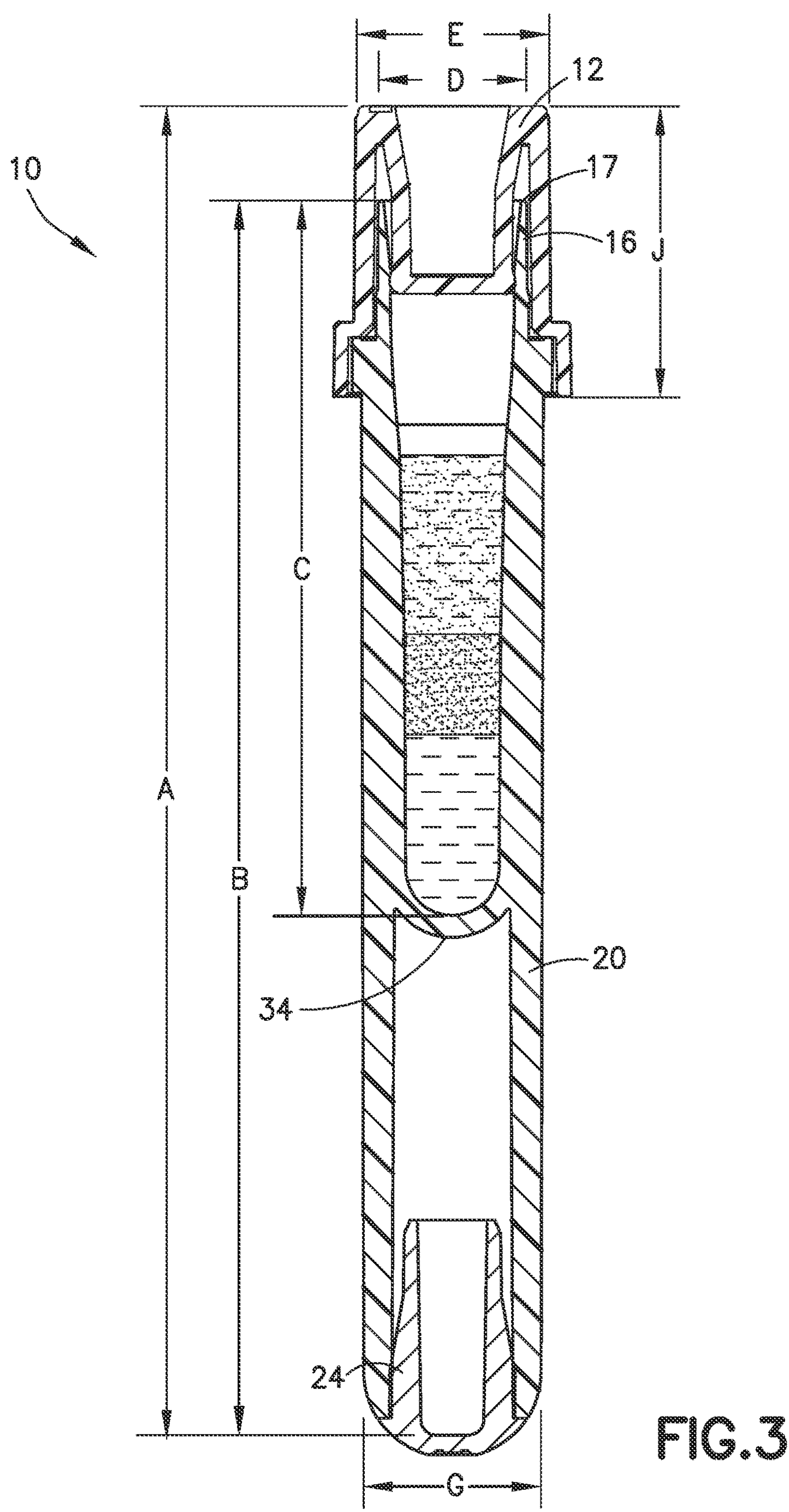
FIG. 3 is another side-cross-sectional view of the capillary collection container assembly of FIG. 1 showing various dimensions of the assembly.

Next, referring to FIG. 3, various dimensions of collection container assembly 10 in accordance with an aspect of the present disclosure are shown. It is to be understood that the dimensions provided are merely illustrative of some embodiments, and that the collection container assembly 10 is not limited as to such ranges. Table 1, shown below, provides the various dimensional ranges in accordance with one embodiment:

TABLE 1

| Dimension Identifier | Part Features | Nominal Dimensions (mm) |
|---|---|---|
| A | Tube Length L1 w/cap | 75-95 |
| B | Tube Length L2 w/o cap | 70-90 |
| C | Tube Interior Reservoir Length | 35-55 |
| D | Tube Opening ID1 | 5-12 |
| E | Tube Opening OD1 | 5-12 |
| F | Tube Bottom ID2 | 3-9 |
| G | Tube Bottom OD2 | 7-15 |
| H | Tube OD | 10-15 |
| J | Cap Height | 15-25 |

As is evident from the dimensions shown and described with respect to FIG. 3 and Table 1, the overall length of interior reservoir 28 (C) is far smaller than the overall length of the collection tube 14 (B), thereby enabling the collection tube 14 to handle a small volume specimen, yet maintain a conventional form factor for use with standard medical testing instruments and/or automation processes. Furthermore, as the tube bottom inner diameter (F) is significantly smaller than the tube opening inner diameter (D), resulting in a tapered sidewall 18, a taller column of blood or specimen is provided, allowing for improved visibility of the specimen, specimen collection, and/or barrier separation between specimen components.

Figures 4A, 4B, 4C:
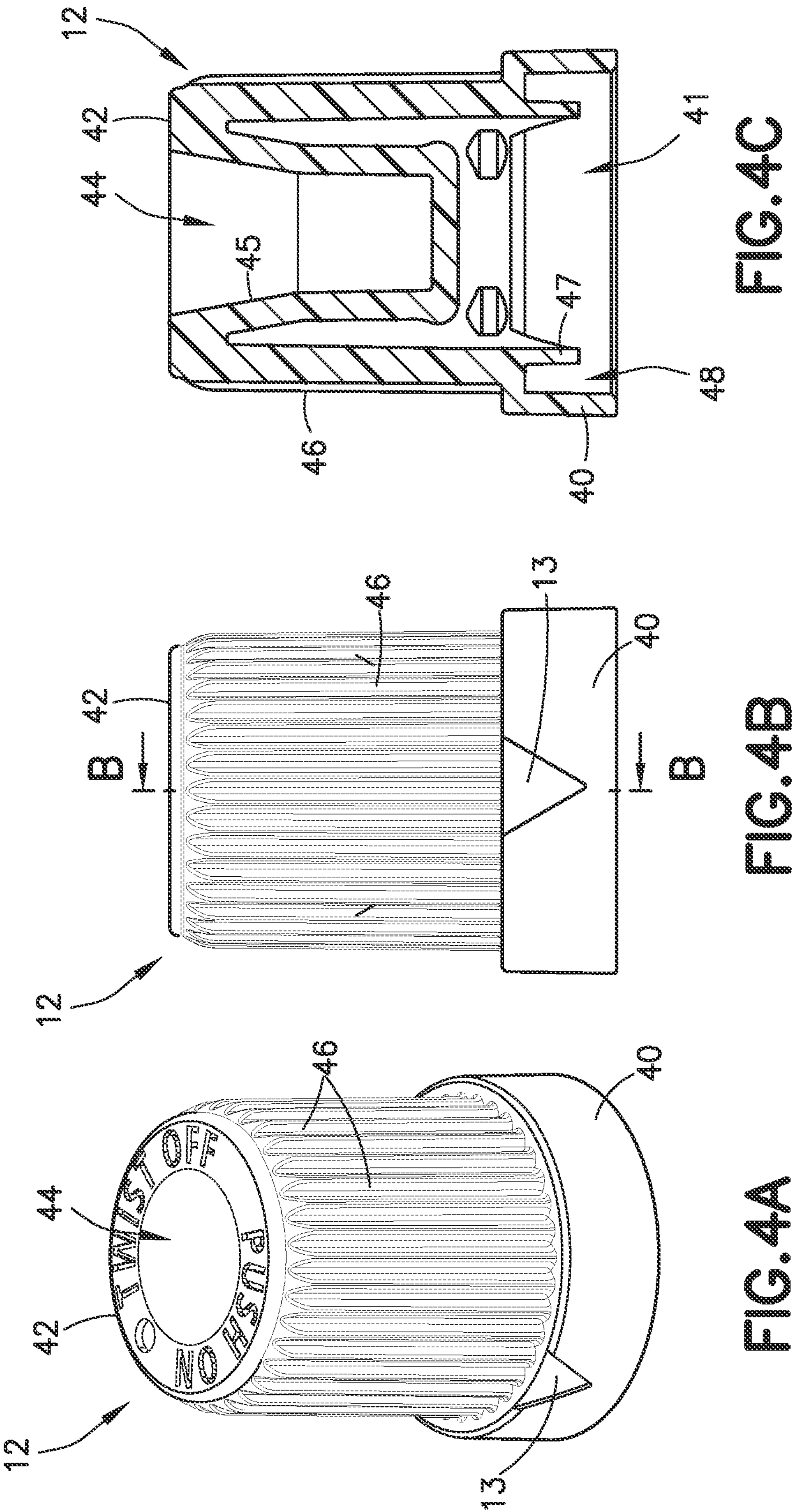
FIG. 4A is a perspective view of a cylindrical cap for use with the capillary collection container assembly of FIG. 1.
FIG. 4B is a side view of the cap of FIG. 4A.
FIG. 4C is a cross-sectional view of the cap of FIG. 4B along line B-B.

Next, referring to FIGS. 4A-4C, details of the cap 12 in accordance with an aspect of the present disclosure are shown. The cap 12 is configured to be substantially cylindrical in shape, with a bottom annular portion 40 defining an opening 41, as well as a top annular surface 42. Extending between the top annular surface 42 and the bottom annular portion 40 are a plurality of vertically-extending ribs 46. The ribs 46 may extend 360° around the cap 12 so as to provide for easy gripping and de-capping during automated handling, when compared with conventional caps having a generally cylindrical shape and/or a rib placement that extends less than 360° around the cap. However, it is to be understood that more or fewer ribs 46 than that which is shown in FIGS. 4A-4C may be utilized. Additionally, the draft angle of the cap 12 may provide for improved gripping of the cap 12 during automated "pick-and-place" gripping and/or de-capping processes, as does the axisymmetric design and diameter of the ribbed portion of the cap 12.

Referring specifically to FIG. 4C, a cross-sectional view of cap 12 is shown. Interior to the top annular surface 42, cap 12 may include a cavity portion 44 defined by a sidewall 45. The cavity portion 44 and sidewall 45 may be sized and configured so as to fit within an inner diameter of the upper mouth portion 16 of the collection tube 14 shown and described with respect to FIGS. 1-3, thereby effectively closing/sealing the opening of the upper mouth portion 16 when the cap 12 is provided on the collection tube 14.

Furthermore, adjacent to the bottom annular portion 40, the cap 12 may further include a downwardly extending sidewall portion 47, which creates a gap 48 between the bottom annular portion 40 and the sidewall portion 47. While not shown, the cap 12 may be held in place on the collection tube 14 via a snap groove on the cap 12 and/or the collection tube 14, with the snap groove providing audible and/or tactile feedback to the user to confirm that the cap 12 is secured to the collection tube 14. Furthermore, a cap pedestal of cap 12 may be utilized to effectively seal the contents of the interior reservoir 28 within the collection container assembly 10. While the interface between cap 12 and collection tube 14 is described herein as a snap fit, it is to be understood that cap 12 and/or collection tube 14 may be coupled by any appropriate method such as, e.g., a threaded interface, a bayonet interface, etc.

Figure 5A:
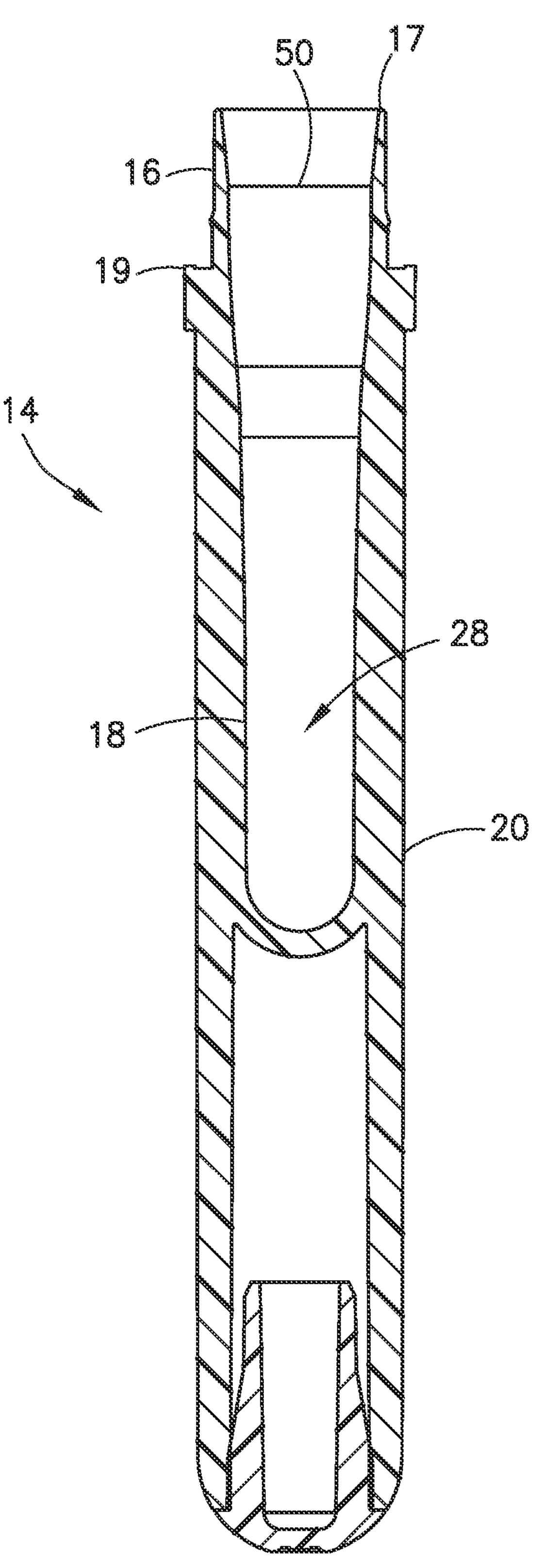
FIG. 5A is a cross-sectional view of a collection tube for use with the capillary collection container assembly of FIG. 1 in accordance with an aspect of the present disclosure.
Figure 5B:
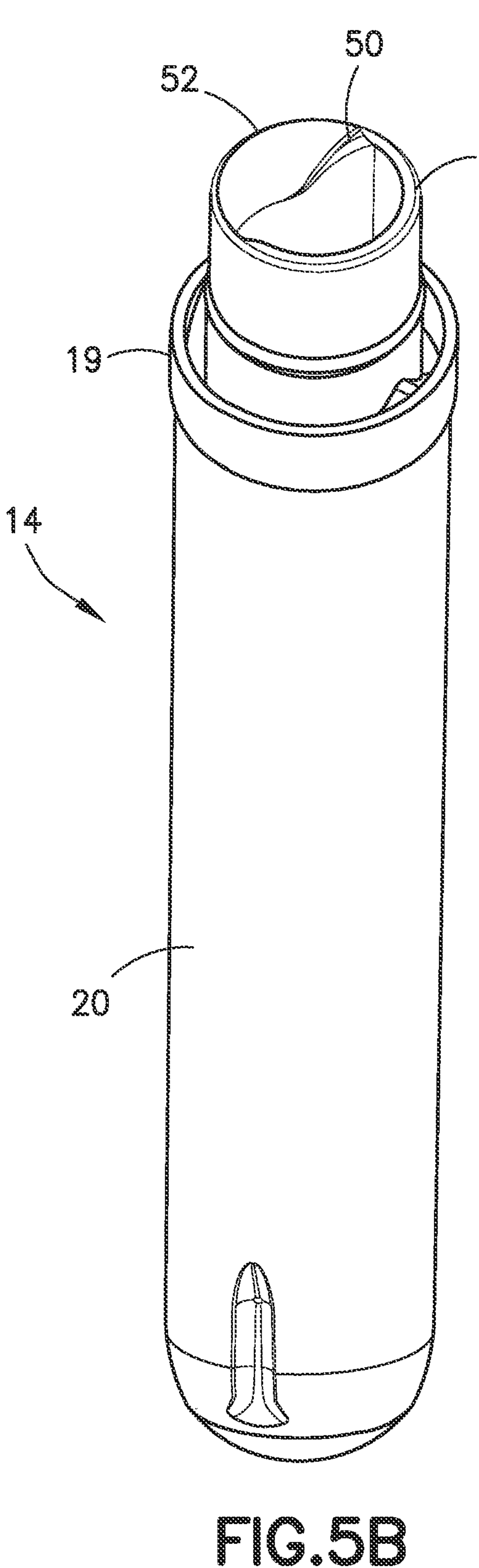
FIG. 5B is a perspective view of the collection tube of FIG. 5A.
Figure 5C:
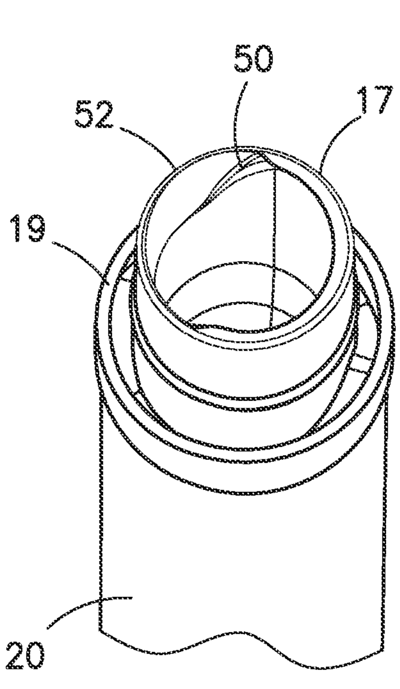
FIG. 5C is perspective view of an opening and mouth of the collection tube of FIG. 5A.

Referring now to FIGS. 5A-5C, collection tube 14 in accordance with one aspect of the present disclosure is shown in further detail.

As described above, many prior art collection tubes have included one or more "scoop" features on or about the top lip portion of the collection tube. These scoops typically extended above the top lip portion, providing a guide for the user to collect a blood sample into the collection tube. However, such scoops were often disadvantageous in that they made collection of an appropriate amount of the sample difficult at times, complicated the manufacturing process and/or tooling of the collection tube, and/or made tube-type identification on automated systems difficult, as most systems could not easily recognize such a collection tube.

However, as shown in FIGS. 5A-5C, the collection tube 14 includes an open lip portion 17 that is uniform (i.e., flat) along its entire circumference, thereby avoiding the various disadvantages of the prior art collection tubes utilizing extended scoop(s). Instead of an extended scoop(s), collection tube 14 includes a natural angle in the tube to assist flow, a substantially V-shaped channel 50 formed in the interior surface of upper mouth portion 16, with the channel 50 narrowing as it extends from the open lip portion 17 toward the interior reservoir 28 of the collection tube 14. To provide for such a configuration, the thickness of a channel lip portion 52 located within the channel 50 is less than the thickness of the other regions of the open lip portion 17. The reduced thickness of the channel lip portion 52 and the V-shaped aspect of the channel 50 provides the user with a clear indication as to what portion of the collection tube 14 should be utilized to acquire a blood or specimen sample.

In utilizing channel 50 as a "scoop", a user is able to effectively acquire a blood sample such that a sufficient amount of the sample is captured within the interior reservoir 28. Furthermore, because the open lip portion 17 is flat across its entire circumference, the formation/manufacture of the collection tube 14 is simplified.

Also, the collection tube 14 may be compatible with most existing tube-type identification and recognition systems. That is, tube-type identification and recognition systems generally comprise vision/camera systems, which are taught to read unique tube outer profiles, thereby recognizing and sorting the tubes appropriately for further analytical processing. By providing a flat open lip portion 17, as well as a distinctive shoulder and nose profile, collection tube 14 aids this machine learning process by allowing a similar, axisymmetric profile to be read, regardless of how the collection tube 14 is rotated and/or placed in, e.g., a storage rack. Such a recognizable profile cannot be created for a collection tube with highly variable outer profiles, as what would be captured by the vision/camera systems would be heavily dependent upon tube rotation at the time of reading. In addition, the outer geometry of collection tube 14 may itself be sufficiently unique as compared to other collection tubes, making it easier to for the tube-type identification and recognition systems to identify and tag the collection tube 14 as a small volume collection tube (and process accordingly).

Figure 6:
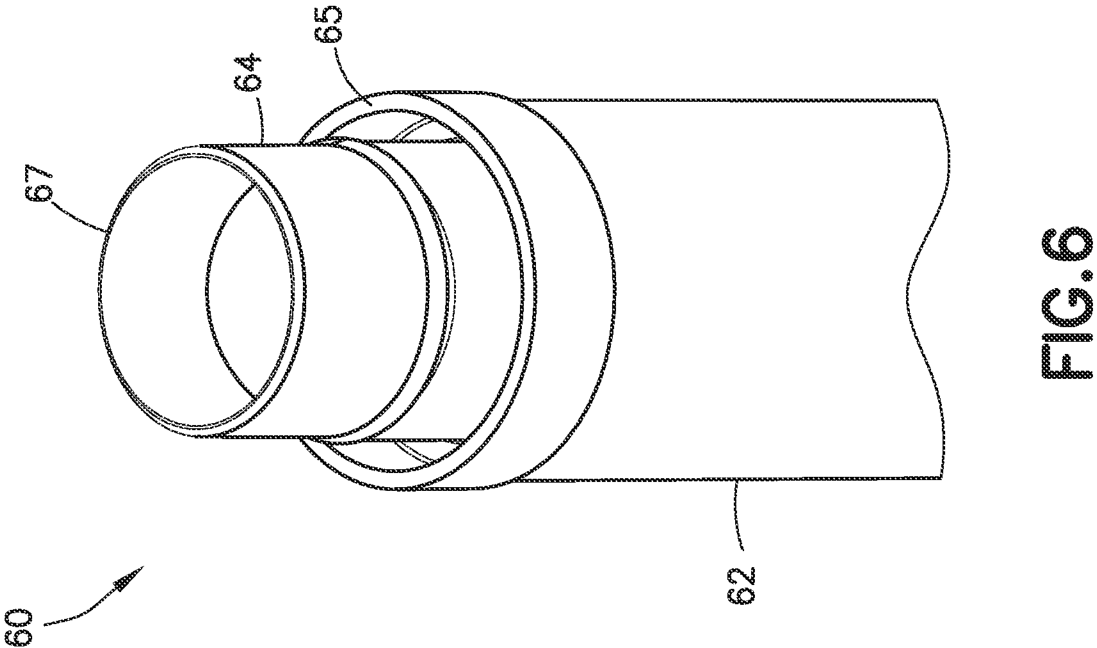
FIG. 6 is a perspective view of an opening and mouth of a collection tube in accordance with another aspect of the present disclosure.

Next, referring to FIG. 6, a collection tube 60 in accordance with another aspect of the present disclosure is shown. Collection tube 60 is defined by an exterior sidewall 62 extending from an open tube bottom (not shown) to an open lip portion 67. While not shown in FIG. 6, it is to be understood that an interior reservoir is defined within collection tube 60, similar to interior reservoir 28 described above with respect to FIGS. 1-3. Furthermore, collection tube 60 includes an upper mouth portion 64 leading to the interior reservoir, as well as an outer lip portion 65 configured for engagement with a cap (not shown).

Unlike collection tube 14 described above with respect to FIGS. 5A-5C, which utilized a V-shaped channel as a scoop, collection tube 60 provides for a 360° scoop configuration, wherein the entire circumference of open lip portion 67 may act as a scoop for the acquisition of a specimen sample. In some embodiments, the open lip portion 67 may be tapered and may have a thickness that is substantially less than the remainder of the wall thickness of upper mouth portion 64. For example, the wall thickness at open lip portion 67 may be between 0.3 mm-0.6 mm, while the wall thickness of other portions of the upper mouth portion 64 may be between 0.75 mm-1.25 mm. In this way, the user may use any part of the open lip portion 67 to acquire the specimen sample. As the open lip portion 67 is flat across its entire circumference, the formation/manufacture of the collection tube 60 is greatly simplified, and the collection tube 60 is more compatible with existing tube recognition systems.

Figure 7:
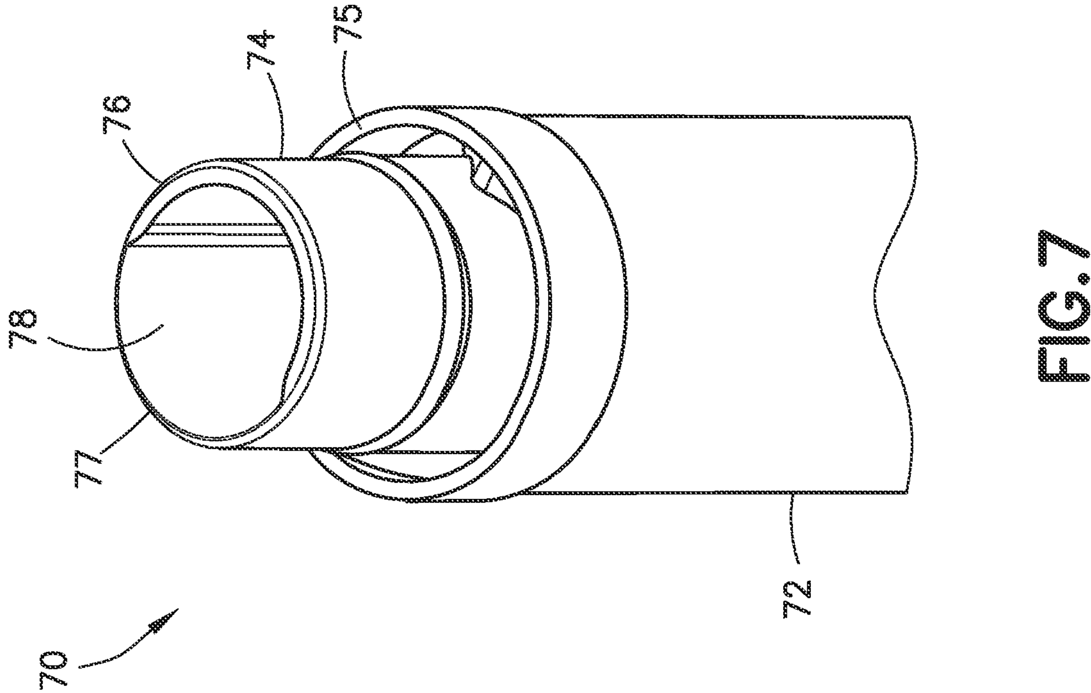
FIG. 7 is a perspective view of an opening and mouth of a collection tube in accordance with another aspect of the present disclosure.

Referring now to FIG. 7, a collection tube 70 in accordance with another aspect of the present disclosure is shown. Collection tube 70 is defined by an exterior sidewall 72 extending from an open tube bottom (not shown) to an open lip portion 76. While not shown in FIG. 7, it is to be understood that an interior reservoir is defined within collection tube 70, similar to interior reservoir 28 described above with respect to FIGS. 1-5C. Furthermore, collection tube 70 includes an upper mouth portion 74 leading to the interior reservoir, as well as an outer lip portion 75 configured for engagement with a cap (not shown).

As shown in FIG. 7, the open lip portion 76 is uniform (i.e., flat) along its entire circumference, thereby avoiding the various disadvantages of the collection tubes utilizing extended scoop(s). Instead of an extended scoop(s), collection tube 70 includes a substantially U-shaped channel 78 formed in the interior surface of upper mouth portion 74, with the channel 78 being uniform as it extends from the open lip portion 76 toward the interior reservoir (not shown) of the collection tube 70. To provide for such a configuration, the thickness of a channel lip portion 77 bound by the channel 78 is less than the thickness of the other regions of the open lip portion 76. The reduced thickness of the channel lip portion 77 and channel 78 provides the user with a clear indication as to what portion of the collection tube 70 should be utilized to acquire a blood or specimen sample. Furthermore, as the open lip portion 76 is flat across its entire circumference, the formation/manufacture of the collection tube 70 is greatly simplified, and the collection tube 70 is more compatible with existing tube recognition systems.

Figure 8:
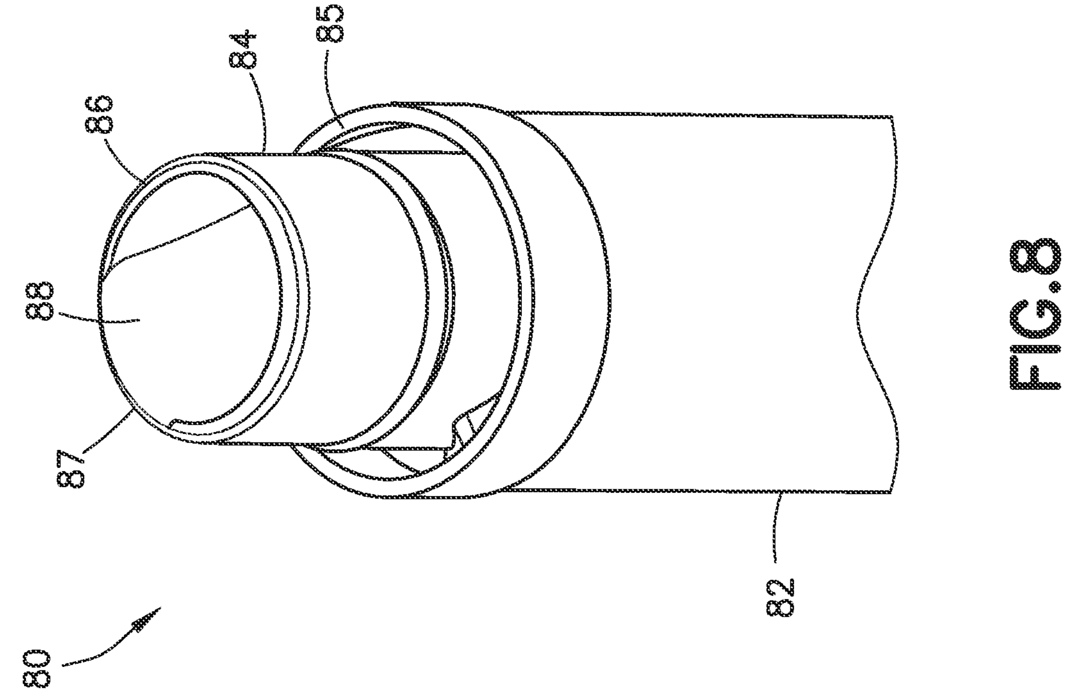
FIG. 8 is a perspective view of an opening and mouth of a collection tube in accordance with another aspect of the present disclosure.

Next, referring to FIG. 8, a collection tube 80 in accordance with another aspect of the present disclosure is shown. Collection tube 80 is defined by an exterior sidewall 82 extending from an open tube bottom (not shown) to an open lip portion 86. While not shown in FIG. 8, it is to be understood that an interior reservoir is defined within collection tube 80, similar to interior reservoir 28 described above with respect to FIGS. 1-3. Furthermore, collection tube 80 includes an upper mouth portion 84 leading to the interior reservoir, as well as an outer lip portion 85 configured for engagement with a cap (not shown).

As shown in FIG. 8, the open lip portion 86 is uniform (i.e., flat) along its entire circumference. Thus, instead of an extended scoop(s) projecting from the open lip portion 86, collection tube 80 includes an "S-curved" channel 88 formed in the interior surface of upper mouth portion 84. Such an "S-curved" channel allows the acquired specimen to flow from the open lip portion 86 toward the interior reservoir (not shown) of the collection tube 80, and provides a visually-distinct "scoop" for the user.

To provide for such a configuration, the thickness of a channel lip portion 87 bound by the channel 88 is less than the thickness of the other regions of the open lip portion 86. Again, the reduced thickness of the channel lip portion 87 and channel 88 provides the user with a clear indication as to what portion of the collection tube 80 should be utilized to acquire a blood or specimen sample. Furthermore, as the open lip portion 86 is flat across its entire circumference, the formation/manufacture of the collection tube 80 is greatly simplified, and the collection tube 80 is more compatible with existing tube recognition systems.

Figure 9:
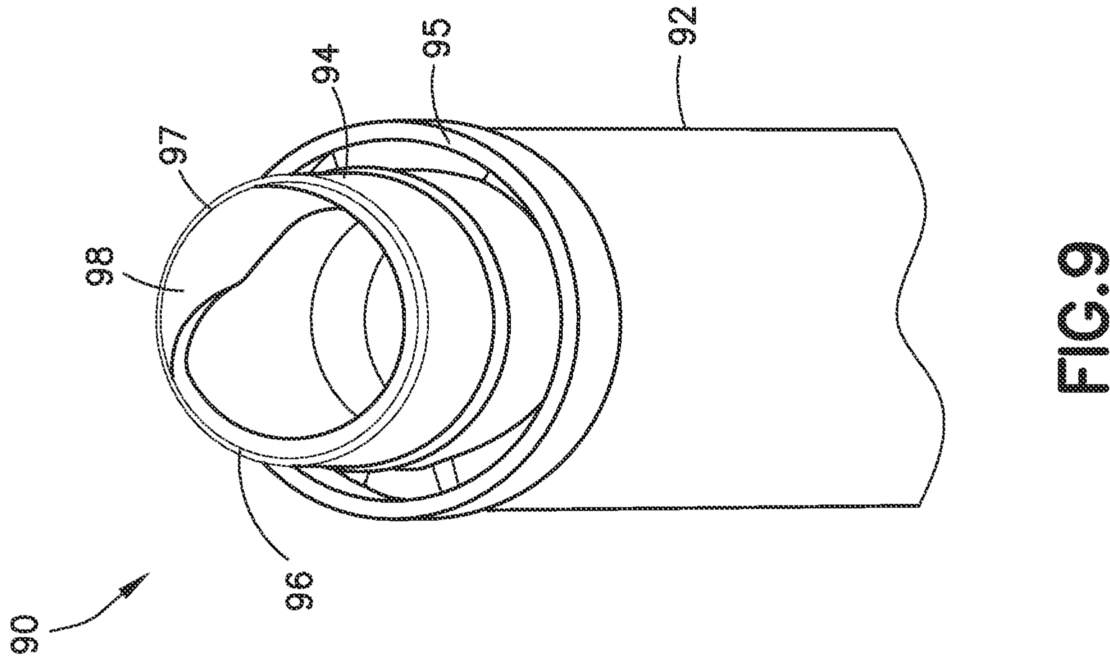
FIG. 9 is a perspective view of an opening and mouth of a collection tube in accordance with another aspect of the present disclosure.

Referring now to FIG. 9, a collection tube 90 in accordance with another aspect of the present disclosure is shown. Collection tube 90 is defined by an exterior sidewall 92 extending from an open tube bottom (not shown) to an open lip portion 96. While not shown in FIG. 9, it is to be understood that an interior reservoir is defined within collection tube 90, similar to interior reservoir 28 described above with respect to FIGS. 1-3. Furthermore, collection tube 90 includes an upper mouth portion 94 leading to the interior reservoir, as well as an outer lip portion 95 configured for engagement with a cap (not shown).

As shown in FIG. 9, the open lip portion 96 is uniform (i.e., flat) along its entire circumference. Thus, instead of an extended scoop(s) projecting from the open lip portion 96, collection tube 96 includes a "reverse S-curved" channel 98 formed in the interior surface of upper mouth portion 98. Such a "reverse S-curved" channel is similar to "S-curved channel 88 described above, but simply reverses the curvature of the channel walls. Channel 98 allows the acquired specimen to flow from the open lip portion 96 toward the interior reservoir (not shown) of the collection tube 90, and provides a visually-distinct "scoop" for the user.

To provide for such a configuration, the thickness of a channel lip portion 97 bound by the channel 98 is less than the thickness of the other regions of the open lip portion 96. This reduced thickness of the channel lip portion 97 and channel 98 provides the user with a clear indication as to what portion of the collection tube 90 should be utilized to acquire a blood or specimen sample. Furthermore, as the open lip portion 96 is flat across its entire circumference, the formation/manufacture of the collection tube 90 is greatly simplified, and the collection tube 90 is more compatible with existing tube recognition systems.

Next, referring to FIGS. 10-14, various embodiments for closing the bottom of the collection tube via, e.g., a plug are shown.

Figure 10:
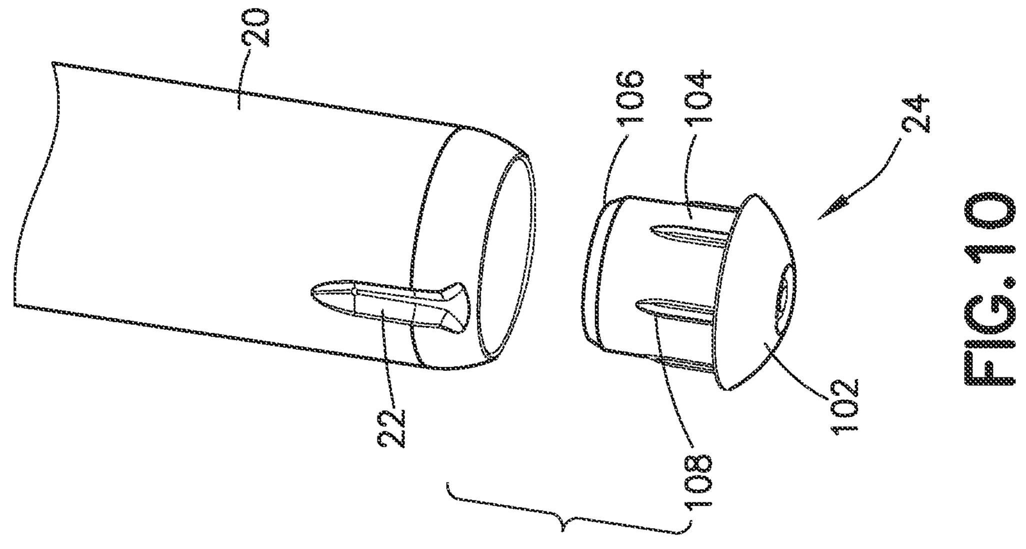
FIG. 10 is an exploded perspective view of a bottom plug for use with a collection tube in accordance with an aspect of the present disclosure.

Referring first to FIG. 10, plug 24 as described above with respect to FIGS. 1-3 is shown in further detail. Specifically, plug 24 may include a rounded bottom portion 102, a substantially-cylindrical body portion 104, and a tapered end portion 106. A plurality of ribs 108 may extend along at least a portion of the body portion 104. In some embodiments, the ribs 108 may be deflectable so as to act as crushed ribs when compressed, thereby providing for a greater interference fit.

In order to close the open tube bottom 22 of the collection tube 14, the plug 24 may be pressed into the open tube bottom 22 until a shoulder surface of the rounded bottom portion 102 meets the open tube bottom 22. The tapered end portion 106 may enable easier initial entry into the open tube bottom 22, and the ribs 108 and/or sidewall of the body portion 104 may provide for an interference fit with the collection tube 14. In this way, the bottom of the collection tube 14 may be closed and provided with a rounded bottom, thereby enabling the collection tube 14 to be compatible with standard testing instruments and/or automation processes.

Figure 11:
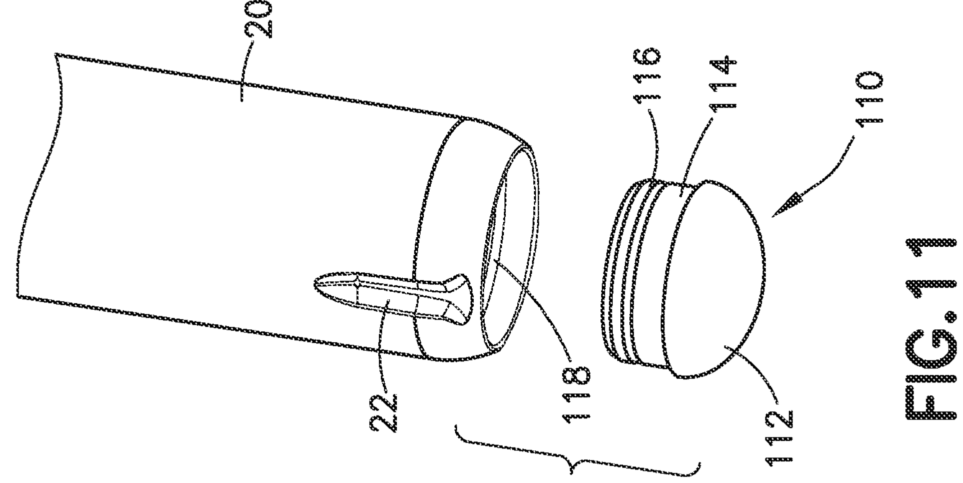
FIG. 11 is an exploded perspective view of a bottom plug for use with a collection tube in accordance with another aspect of the present disclosure.

Referring now to FIG. 11, a plug 110 in accordance with another embodiment is shown. Similar to plug 24 described above, plug 110 includes a rounded bottom portion 112 and a substantially-cylindrical body portion 114. However, as opposed to a plurality of ribs, the plug 110 includes an inset ring 116 positioned annularly around the body portion 114. The ring 116 is configured to engage a corresponding raised ring 118 positioned within the sidewall 20 of the collection tube 14 proximate the open tube bottom 22. In this way, the interface between the inset ring 116 and raised ring 118 provides for a "snap" or "click" feedback when the plug 110 is fully inserted into the open tube bottom 22. It is to be understood that in alternative embodiments, inset ring 116 may instead be configured to be raised, while raised ring 118 may be configured to be inset.

In order to close the open tube bottom 22 of the collection tube 14, the plug 110 may be pressed into the open tube bottom 22 until the inset ring 116 and the raised ring 118 engage. In this way, the bottom of the collection tube 14 may be closed and provided with a rounded bottom, thereby enabling the collection tube 14 to be compatible with standard testing instruments and/or automation processes.

Figure 12:
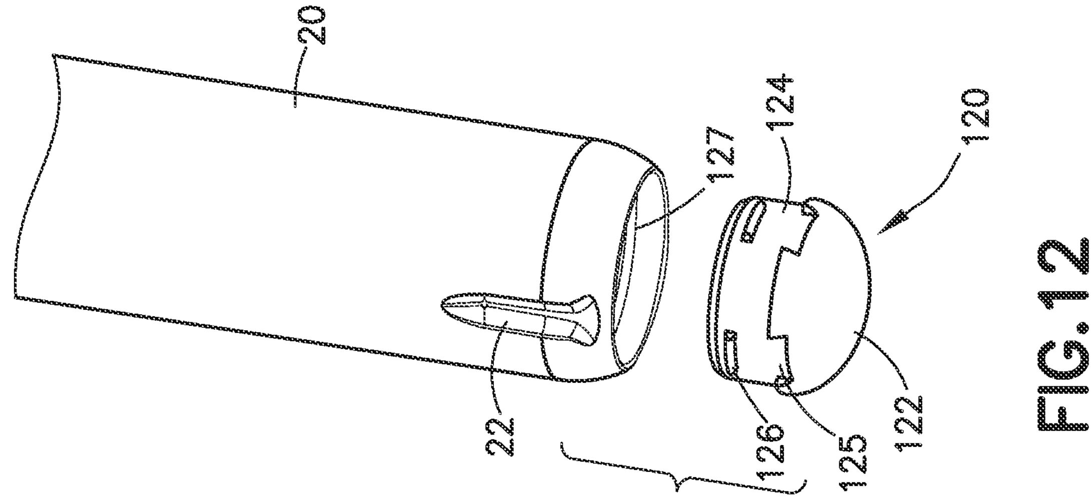
FIG. 12 is an exploded perspective view of a bottom plug for use with a collection tube in accordance with another aspect of the present disclosure.

Next, referring to FIG. 12, a plug 120 in accordance with another embodiment is shown. Similar to plug 110 described above, plug 120 includes a rounded bottom portion 122 and a substantially-cylindrical body portion 124, and is configured for a snap-fit connection with the collection tube 14. However, as opposed to an inset ring on the body portion 124, plug 120 includes a plurality of raised tabs 126 positioned annularly around the body portion 124. The raised tabs 126 are sized and configured to engage a corresponding inset ring 127 positioned within the sidewall 20 of the collection tube 14 proximate the open tube bottom 22. In this way, the interface between the raised tabs 126 and the inset ring 127 provides for a "snap" or "click" feedback when the plug 120 is fully inserted into the open tube bottom 22. It is to be understood that in alternative embodiments, the raised tabs 126 may instead be configured to be inset, while inset ring 127 may be configured to be raised.

In order to close the open tube bottom 22 of the collection tube 14, the plug 120 may be pressed into the open tube bottom 22 until the raised tabs 126 and the inset ring 127 engage. Cutouts 125 may be provided on the rounded bottom portion 122 for tooled insertion and/or removal of the plug 120. In this way, the bottom of the collection tube 14 may be closed and provided with a rounded bottom, thereby enabling the collection tube 14 to be compatible with standard testing instruments and/or automation processes.

Figure 13:
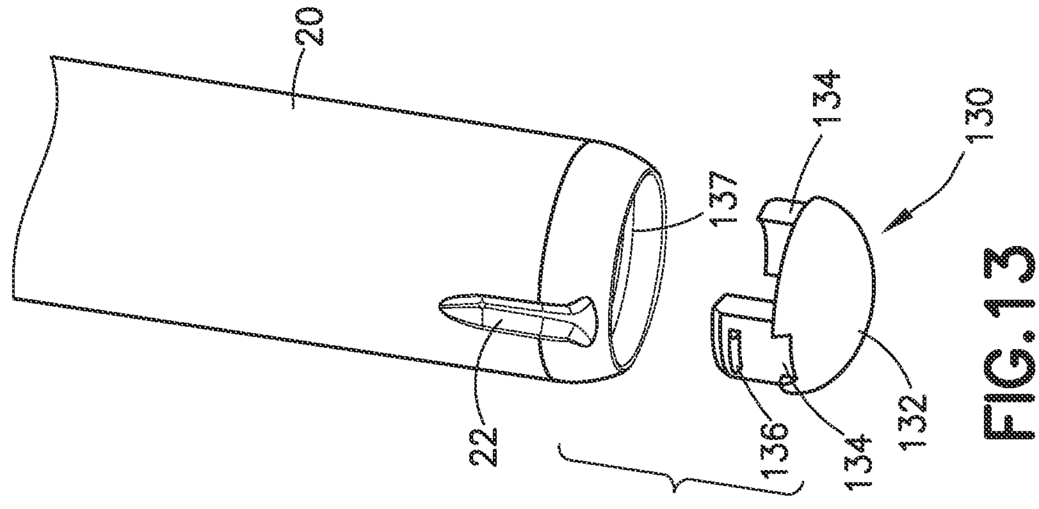
FIG. 13 is an exploded perspective view of a bottom plug for use with a collection tube in accordance with another aspect of the present disclosure.

Referring now to FIG. 13, a plug 130 in accordance with another embodiment is shown. Similar to plug 120 described above, plug 130 includes a bottom portion 132 and is configured for a snap-fit connection with the collection tube 14 by way of raised tabs and an inset ring. However, as opposed to a substantially-cylindrical body 124, plug 130 includes a pair of flanges 134 having raised tabs 136 extending therefrom. The raised tabs 136 are sized and configured to engage a corresponding inset ring 137 positioned within the sidewall 20 of the collection tube 14 proximate the open tube bottom 22. In this way, the interface between the raised tabs 136 and the inset ring 127 provides for a "snap" or "click" feedback when the plug 130 is fully inserted into the open tube bottom 22. It is to be understood that in alternative embodiments, the raised tabs 136 may instead be configured to be inset, while inset ring 137 may be configured to be raised.

The flanges 134 provide for reduced hoop stress on the collection tube 14 as compared to a fully cylindrical body. Furthermore, unlike plugs 24, 110, and 120 described above, the plug 130 include a partially flattened bottom surface 132, which is desirable in some cases due to the ability to stand the collection tube 14 in an upright position after a collection procedure is complete. In particular, providing a plug 130 with a partially flattened bottom surface 132 may be particular advantageous in a special care setting, where a standard rack to hold the tube(s) may be unavailable.

In order to close the open tube bottom 22 of the collection tube 14, the plug 130 may be pressed into the open tube bottom 22 until the raised tabs 136 and the inset ring 137 engage. In this way, the bottom of the collection tube 14 may be closed and provided with a rounded bottom, thereby enabling the collection tube 14 to be compatible with standard testing instruments and/or automation processes.

Figure 14:
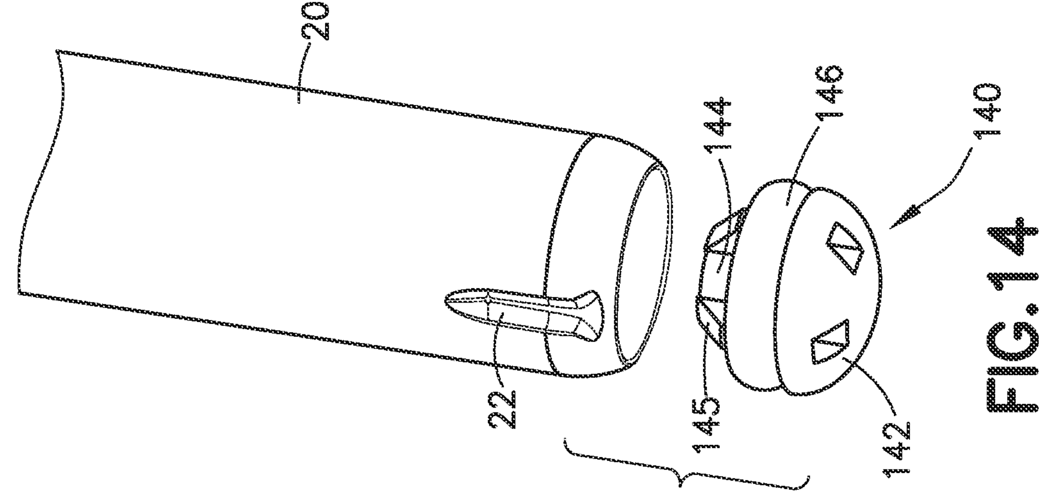
FIG. 14 is an exploded perspective view of a bottom plug for use with a collection tube in accordance with another aspect of the present disclosure.

Next, referring to FIG. 14, a plug 140 in accordance with another embodiment is shown. Plug 140 may include a substantially rounded bottom portion 142, and may be retained within the collection tube 14 by way of an elastomeric O-ring 146. The O-ring 146 may be positioned around a substantially cylindrical stud 144 extending from the rounded bottom portion 142. The stud 144 may include a plurality of angled prongs 145 extending therefrom, with the prongs 145 configured to hold the O-ring 146 in place in conjunction with a shoulder surface of the bottom portion 142.

In order to close the open tube bottom 22 of the collection tube 14, the plug 140 may be pressed into the open tube bottom 22 until a shoulder surface of the rounded bottom portion 142 meets the open tube bottom 22, with the O-ring 146 sized and configured to provide an interference fit with the collection tube 14. In this way, the bottom of the collection tube 14 may be closed and provided with a rounded bottom, thereby enabling the collection tube 14 to be compatible with standard testing instruments and/or automation processes.

The collection containers described above with respect to FIGS. 1-14 may be usable with any appropriate automated sample analyzers. Examples of such analyzers include (but are not limited to) the Cobas® P512, Cobas® P612, Cobas® c501, Cobas® c502, Cobas® c602, Cobas® e601, Cobas® e602, Cobas® e801, and/or Cobas® e802 from Roche Diagnostics, the DxA, AU5800, DCX700AU, Dxl, and/or Falcon from Beckman Coulter, Inc., the Atellica® SH, Aptio®, Atellica® CH, and/or Atellica® IA from Siemens Healthcare, the Vitros® from Ortho Clinical Diagnostics, and/or the GLP, a3600, Alinity, and/or Architect from Abbott.

While several embodiments of a device for capillary collection of blood samples were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A specimen collection container assembly comprising:
a collection tube having a first open end and a second open end;
an interior reservoir formed within the collection tube;
a cap configured to be couplable to the collection tube to close the first open end; and
a plug configured to be couplable to the collection tube to close the second open end,
wherein the collection tube further comprises:
a flat lip portion extending 360° around the first open end to define an opening of the first open end; and
a scoop portion formed in the flat lip portion and within an interior wall surface proximate the flat lip portion, with the scoop portion formed at the flat lip portion and extending away therefrom toward the interior reservoir, and with the scoop portion formed about only a portion of a circumference of the flat lip portion;
wherein a thickness of the flat lip portion located in the scoop portion is less than a thickness of a remainder of the flat lip portion outside of the scoop portion.

2. The assembly of claim 1, wherein the interior reservoir tapers from the first open end to a rounded bottom surface formed within the collection tube.

3. The assembly of claim 1, wherein the scoop portion is one of V-shaped, U-shaped, S-shaped, or reverse S-shaped.

4. The assembly of claim 1, wherein the plug is configured to be coupled to the collection tube by way of an interference fit.

5. The assembly of claim 1, wherein the plug is configured to be coupled to the collection tube way a snap-fit connection.

6. A specimen collection tube comprising:
a first open end;
a second open end;
an exterior sidewall;
an interior reservoir formed within the exterior sidewall;
a flat lip portion extending 360° around the first open end to define an opening of the first open end; and
a scoop portion formed in the flat lip portion and within an interior wall surface proximate the flat lip portion, with the scoop portion formed at the flat lip portion and extending away therefrom toward the interior reservoir, and with the scoop portion formed about only a portion of a circumference of the flat lip portion;
wherein a thickness of the flat lip portion located in the scoop portion is less than a thickness of a remainder of the flat lip portion outside of the scoop portion.

7. The specimen collection tube of claim 6, wherein the interior reservoir tapers from the first open end to a rounded bottom surface.

8. The specimen collection tube of claim 6, wherein the scoop portion is one of V-shaped, U-shaped, S-shaped, or reverse S-shaped.

9. The specimen collection tube of claim 6, wherein the scoop portion comprises a channel formed in the interior wall surface, the channel extending from the flat lip portion down toward the interior reservoir.

10. The specimen collection tube of claim 9, wherein the channel narrows as it extends from the flat lip portion down toward the interior reservoir.

11. The specimen collection tube of claim 9, wherein the channel is uniform as it extends from the flat lip portion down toward the interior reservoir.

12. The assembly of claim 1, wherein the scoop portion comprises a channel formed in the interior wall surface, the channel extending from the flat lip portion down toward the interior reservoir.

13. The assembly of claim 12, wherein the channel narrows as it extends from the flat lip portion down toward the interior reservoir.

14. The assembly of claim 12, wherein the channel is uniform as it extends from the flat lip portion down toward the interior reservoir.

15. The assembly of claim 1, wherein the portion of the circumference of the flat lip portion about which the scoop portion is formed is less than 360°.

16. The specimen collection tube of claim 6, wherein the portion of the circumference of the flat lip portion about which the scoop portion is formed is less than 360°.

* * * * *